United States Patent
Hamburg

(10) Patent No.: US 11,000,404 B2
(45) Date of Patent: May 11, 2021

(54) ORAL APPLIANCE

(71) Applicant: Richard D. Hamburg, Setauket, NY (US)

(72) Inventor: Richard D. Hamburg, Setauket, NY (US)

(*) Notice: Subject to any disclaimer, the term of this patent is extended or adjusted under 35 U.S.C. 154(b) by 594 days.

(21) Appl. No.: 15/909,770

(22) Filed: Mar. 1, 2018

(65) Prior Publication Data

US 2019/0269545 A1 Sep. 5, 2019

(51) Int. Cl.
*A61F 5/56* (2006.01)
*A61C 7/08* (2006.01)

(52) U.S. Cl.
CPC ............... *A61F 5/566* (2013.01); *A61F 5/56* (2013.01); *A61C 7/08* (2013.01)

(58) Field of Classification Search
CPC ...... A61F 5/56; A61F 5/566; A61F 2005/563; A61C 7/08; A63B 71/085
USPC .......................................... 128/848, 861, 862
See application file for complete search history.

(56) References Cited

U.S. PATENT DOCUMENTS

| | | |
|---|---|---|
| 5,066,231 A | 11/1991 | Oxman et al. |
| 5,873,365 A | 2/1999 | Brown |
| 2010/0065066 A1 | 3/2010 | Hamburg |
| 2010/0300458 A1 | 12/2010 | Stubbs et al. |
| 2018/0344511 A1* | 12/2018 | Brown ................... A61F 5/566 |

FOREIGN PATENT DOCUMENTS

| | | | | |
|---|---|---|---|---|
| WO | WO-2016149742 A1 * | 9/2016 | ............. | A61F 5/566 |
| WO | WO-2017149523 A1 * | 9/2017 | ............. | A61F 5/566 |

OTHER PUBLICATIONS

DynaFlex Dorsal, www.dynaflex.com/dental-sleep-laboratory-devices/dorsal, 9 pages, Mar. 15, 2018.
AirwayLabs—Fabricator of the Tap, Airway Labs, 1 page, 2012.
SomnoDent Alpha, Mandible Repositioning Antisnoring Orthosis, SomnoMed, SD Instructions for Use, 20 pgs (date unknown—see explanation on transmittal form).
Respire Blue+, Respire Medical, www.respiremedical.com/respire-blue-plus, 3 pages (Mar. 15, 2018).
SomnoDent Signature and Standard Line, Airway Management, www.somnomed.com (Mar. 15, 2018).

* cited by examiner

*Primary Examiner* — Keri J Nelson

(74) *Attorney, Agent, or Firm* — M.J. Ram and Associates

(57) ABSTRACT

An oral appliance comprises interacting upper and lower dental encasing components formable to overlay portion of the patient's upper and lower teeth. The dental encasings each comprise sheets of a heat softenable and moldable over-mold material on substrates comprising one or more pieces of a stiffening material. The over-mold material is heated to a moderately elevated temperature which will not cause tissue damage when placed in the patient's mouth. While still warm the material can be shaped to conform the patient's teeth but is non-deformable once cooled to body temperature. The stiffening material is non-deformable when heated to the same elevated temperature.

7 Claims, 6 Drawing Sheets

ORAL APPLIANCE

An oral appliance that controls positioning of a patient's jaw and can be shaped to a patient's mouth in a single office visit by the dentist or dental technician is provided. The oral appliance comprises an upper component and a lower component removably connected together, the components linked together in a moveable manner. The dental upper component, formed to overlay at least a portion of the patient's upper teeth and the upper labial surface of the patient's mouth, has at least one ledge extending along the upper labial surface of the upper component. The lower dental component, formed to overlay at least a portion of the patient's lower teeth and the lower lingual surface, has at least one rotating body fixed to the lower labial surface of the second dental component. The at least one rotating body and the at least one ledge are disposed in positions on their respective labial surfaces to enable the at least one rotating body to contact and rotate along a length of the at least one ledge as the patient's mouth closes, advancing the patient's jaw forward.

BACKGROUND

Field of the Invention

The oral appliance is designed for the prevention of snoring and obstructive sleep apnea.

Description of the Related Art

Snoring and obstructive sleep apnea occur when there is a partial occlusion in a patient's airway, typically involving the patient's tongue. By advancing the patient's lower jaw forward, the tongue is carried forward and the potential blocking of the patient's airway by the tongue is reduced or prevented. Unblocking the airway results in an increased airflow through the mouth. By unblocking the airway the snoring is decreased and obstructive sleep apnea is prevented.

Applicant's prior filed patent application, published as US Serial Number 2010/0065066 A1 on Mar. 18, 2010, is an example of such an oral appliance. However, that product could not be produced in a single office visit, required preparing molds of the patient's mouth, constructing a model of the patients upper and lower teeth and labial surface, casting a two piece oral appliance from molten thermoplastic polymers and then, in a separate office visit, adapting the two piece oral appliance to the patient's teeth. Further, because the appliance was formed from a hard plastic, it was difficult to modify or adjust the appliance.

Another device for use in treating sleep apnea is the SomnoDent® Fusion™ (SomnoMed, Plano, Tex.) The dentist/dental technician prepares a bite impression of the patient's mouth using a standard dental impression procedure such as described below. That bite impression is the sent to SomnoMed which prepares the oral appliance compatible with the impression, the appliance being fabricated from an acrylic material which is not amenable to molding and reshaping in the patient's mouth.

Another device provided by SomnoMed, referred to as the SomnoDent® Alpha is designed as a temporary appliance for patients prior to receiving a permanent one from the dentist. The Somno Dent® Alpha is limited to 90 days of use before a replacement is required. It consists of a one-piece lower tray which has removable and adjustable wings and a one-piece upper tray with removable and adjustable lugs. Each tray includes a proprietary heat formable inner liner material. The liner material must be heated to 95° C./203° F. before being placed in the patient's mouth. This minimum temperature requirement creates risks for the patient of third degree burns of the tongue or gum tissue caused by exposure to temperatures over 140 degrees Fahrenheit for just five seconds. On the other hand, allowing the device heated to 203° F. to cool to a safe temperature before placing in the patient's mouth can severely interfere with the dentist's ability to conform the liner to the patient's teeth. Also, the Somnomed Alpha design is not indicated as suitable for use in a large class of patients such as those with excessive crossbite. While the amount of crossbite that can be treated has not been described, any significant width of the posterior mandibular molars will significantly affect the ability of the wing\lug contact. In addition, the Somnodent Alpha outer shell is constructed out of a single piece, fixed shape polycarbonate material. This structural element limits the proprietary heat formable inner liner from conforming to patients with a significant crossbite.

The DynaFlex® Dorsa Appliance, a similarly appearing device used for treating snoring and obstructive sleep apnea, constructed out of acrylic materials by DynaFlex using CAD/CAM digital software on milling machines. These devices cannot be prepared by the dentist/dental technician in the dental office and are fabricated remotely by machining to match the patients bite mold.

The Respire Blue™ device (Respire Medical, Brooklyn N.Y.) is a sleep apnea treatment device featuring two or four interlocking wings, with half of the wings on the upper and half on the and lower half of the appliance. Like the above described devices, this appliance is also fabricated by the company from the initial impression prepared by the dentist.

Another device, provided by Airway Management of Carrolton, Tex., addresses sleep-disordered breathing with a two-part appliance that is fabricated in a single office visit in the dentist's office and can be reheated and refitted. The product comprises hard, fixed shaped polycarbonate upper and lower trays (the liner) which are filled with a heat (160° F.) softenable, thermoplastic acrylic material referred to as "ThermAcryl". The tray carrying the softened ThermAcryl® material is placed in the patients mouth over the teeth and avowed to cool and set. This device does not use wings such as shown in FIGS. 1-3 but instead incorporates a latching structure which holds the upper and lower bite plates together and is located between the front two teeth. That latching structure receives an adjustment screw that protrudes through the front lips for adjusting the relative positions of the upper and lower portions of the appliance, referred to as "mid-line adjustment". If the bite impression needs to be adjusted the recommended procedure is to soften and remove the ThermAcryl from the tray and start over with new material.

Another thermoplastic material that has been used in preparing dental impressions is (U.S. Pat. No. 5,066,231) using a monolayer or bilayer of the polycaprolactone which is solid (stiff) at 38° C. but has a melting or softening temperature below 65° C.

Removable appliances for use in mandibular advancement during sleep are known in the art. The mandibular advancement appliances are typically worn by patients in accordance with instructions from a doctor, dentist or orthodontist. Such appliances are constructed for use on both upper and lower dental arches. Both the upper and lower dental arches include respective engaging surfaces that set the patient's mouth in a position in which the lower jaw is advanced. The respective surfaces may attach the dental arches to each other preventing movement of the jaw during sleep. This attachment may also hold the patient's mouth open to allow for increased airflow during sleep. Non-attached engagements have also been shown in which the surfaces project upwardly from a lower arch and downwardly from an upper arch. The upwardly extending projections are engaged in front of the downwardly extending projections allowing the jaw to open and close while still being held in an advanced position.

When non-attached engagements are used, the rate of mandibular advancement is determined by the angle of the projecting surfaces. Once the surfaces are in contact, the mandibular segment continues to advance forward at a fixed rate until it reaches a maximum position. When the maximum setting is too close to the patient's maximum mandibular protrusion, tension on the Temporal Mandibular Joint (TMJ) can be severe. Tension during the night from the use of non-attached devices can be relieved by the natural yawning process and by increasing the opening position of the jaw. Depending on the shape of the guiding wing surface, the degree of mouth opening does not have to be proportional to the amount of mandibular advancement. Tension on the muscles of mastication is reduced with the reduction in its distance between the origin and insertion of the muscle. So, as the mouth opens, even if adequate mandibular advancement remains, a reduction in muscle tension is experienced. This tension will be further reduced as one moves out of mandibular advancement but such actions reduce the benefit on obstructions. However, relieving the tension by opening the mouth decreases the desired advancement, thus negating any improvement in airway obstruction.

The exact positioning and dimensions of the engaging surfaces are determined when an impression is taken of the patients teeth. However, due to errors in measuring the patient's centric and maximum protrusion position, or due to errors in establishing the relationship of the patient's maxillary arch in three planes of space in order to transfer this information to the dental lab. Dentist can but rarely do use Facebow registration to capture this structural relationships. "[A]pproximately 90% to 95% of all restorations and prostheses are fabricated and other dental procedures are performed using either no articulator or a disposable articulator without a face bow because of misunderstood concepts, complex instrumentation, and time-consuming procedures". (.www.aegisdentalnetwork.com/ida/2012/04/the-use-of-a-face-bow-for-function-and-esthetics)

Because dental laboratories do not use the necessary articulators to maintain these positions, this often results in a misalignment of the maxillary arch and the axis of rotation for proper function and an ill-fitting appliance (one that does not properly alter the normal functional movement of the jaw. Even when adequate registration is taken, errors in lab manufacturing can affect the fit and function of the oral appliance. This may result in an appliance that causes the patient's jaw to twist, resulting in the Mandibular Condyle being more forward on one side than the other, or an appliance that does not provide adequate advancement to compensate for the airway obstruction. A screw mechanism may be utilized to provide adjustments; however, as the jaw advances the contact between the wings and the cam or lug can become inconsistent, especially if the "three plane structural relationships are not maintained". Therefore, screw adjustment mechanism may provide functional contact on only one side of the jaw and not the other side.

A need therefore exists for an appliance that improves the manner in which the mandible is advanced, while also allowing for mandibular advancement adjustments and means for integration with separate elements that assist in the prevention of snoring and obstructive sleep apnea, that appliance being able to be molded to conform to the patient's tooth arrangement during a single visit to the dentist so that the patient on leaving the dentist's office has a fully functional appliance for suitable for its intended purposes.

SUMMARY

The oral appliance described herein is constructed in a single visit to the dentist or dental technician to conform to the patient's upper and lower teeth while addressing at least the above problems and/or disadvantages and to provide at least the advantages described below. Accordingly, an aspect of the present device is to provide an oral appliance for the control of mandibular advancement, said oral appliance being adapted to allow unobstructed flow of air/oxygen into the mouth of the patient.

The improved oral appliance described herein, which provides controlled positioning of a patient's jaw, comprises an upper dental encasing component and a lower dental encasing component, both of which are formed directly in the patient's mouth in a single procedure. The upper dental component overlays at least a portion of the patient's upper teeth including a lingual surface, a labial surface, and at least one ledge extending along the labial surface of the first dental encasing component. A lower dental encasing component overlays at least a portion of the patient's lower teeth and also includes a lingual surface and a labial surface. At least one structure (a rotating body) is provided to fix the lower (first) dental encasing component to the labial surface of the upper (second) dental encasing component. The rotating body and ledge are positioned on their respective labial surfaces to enable the rotating body to contact and rotate along a length of the ledge as the patient's mouth closes, causing the patient's jaw to advance forward.

In contrast to prior oral appliances intended for the same purposes, the appliance set forth herein is constructed of a thermoplastic, malleable materials that can be heated to a suitable temperature and safely formed directly in the patients mouth to conforming the upper and lower teeth and mouth surfaces without risk of exposure to unsafe elevated temperatures. The material of construction is then further cooled to convert the construction material into a non-malleable configuration. E-Beam radiation may also be used to treat the initial moldable material to allow for additional repetitive molding by the dentist if adjustments are needed or dental anatomy changes.

BRIEF DESCRIPTION OF THE DRAWINGS

Aspects, features and advantages of the present invention will become more apparent from the following detailed description when taken in conjunction with the accompanying drawings in which.

DETAILED DESCRIPTION OF THE PREFERRED EMBODIMENTS

Figure 1:
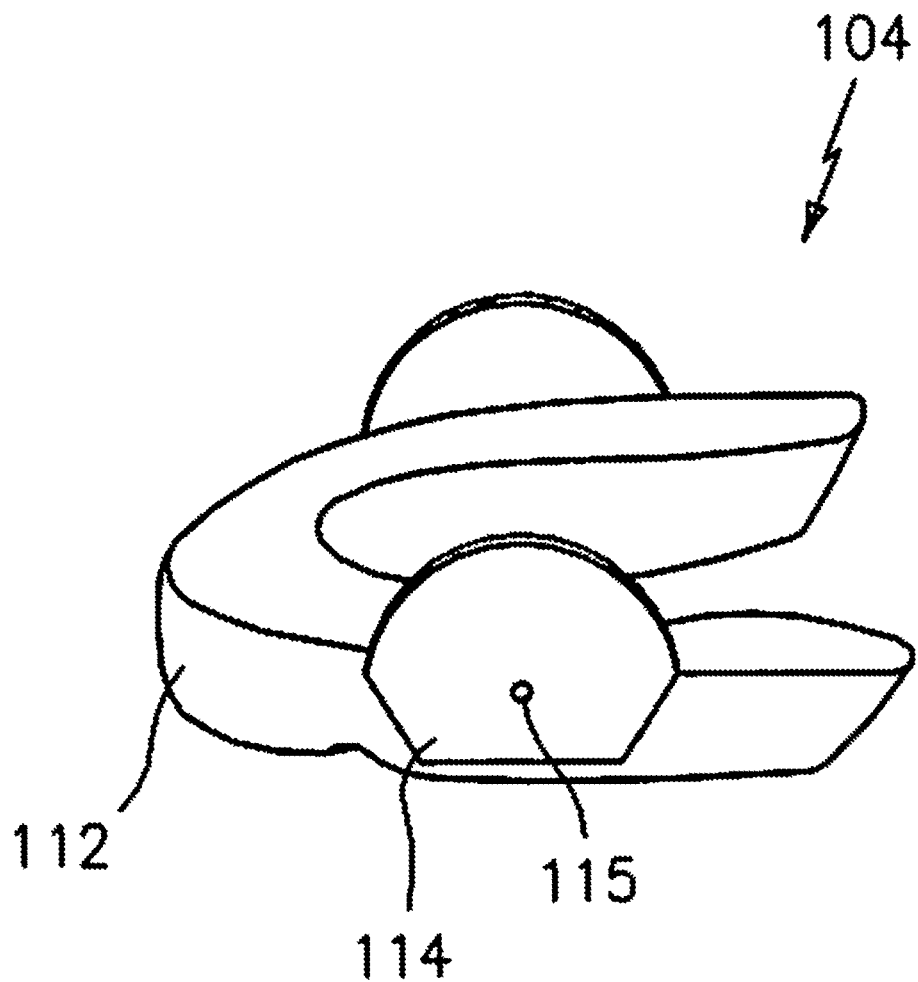
FIGS. 1A and 1B are diagrams illustrating a side view of separated upper and lower dental arches of a prior art oral appliance.

Preferred embodiments of the present invention are described in detail with reference to the accompanying drawings. FIGS. 1A, 1B, 2 and 3 depict a prior art device shown in applicant's earlier filed patent application published as US Application No. 2010/00656066. Said prior application is cited herein as the device shown therein functions in a similar manner as the presently disclosed oral device. However, the presently described and claimed device provides patentable improvements, set forth below, over said prior device and addresses several deficiencies in the design and fabrication thereof. In FIGS. 4-7 the same or similar elements identified in said prior art application are denoted by the same or similar reference numerals even though they are depicted in different drawings and are constructed from different materials that have different properties.

Figure 1B:
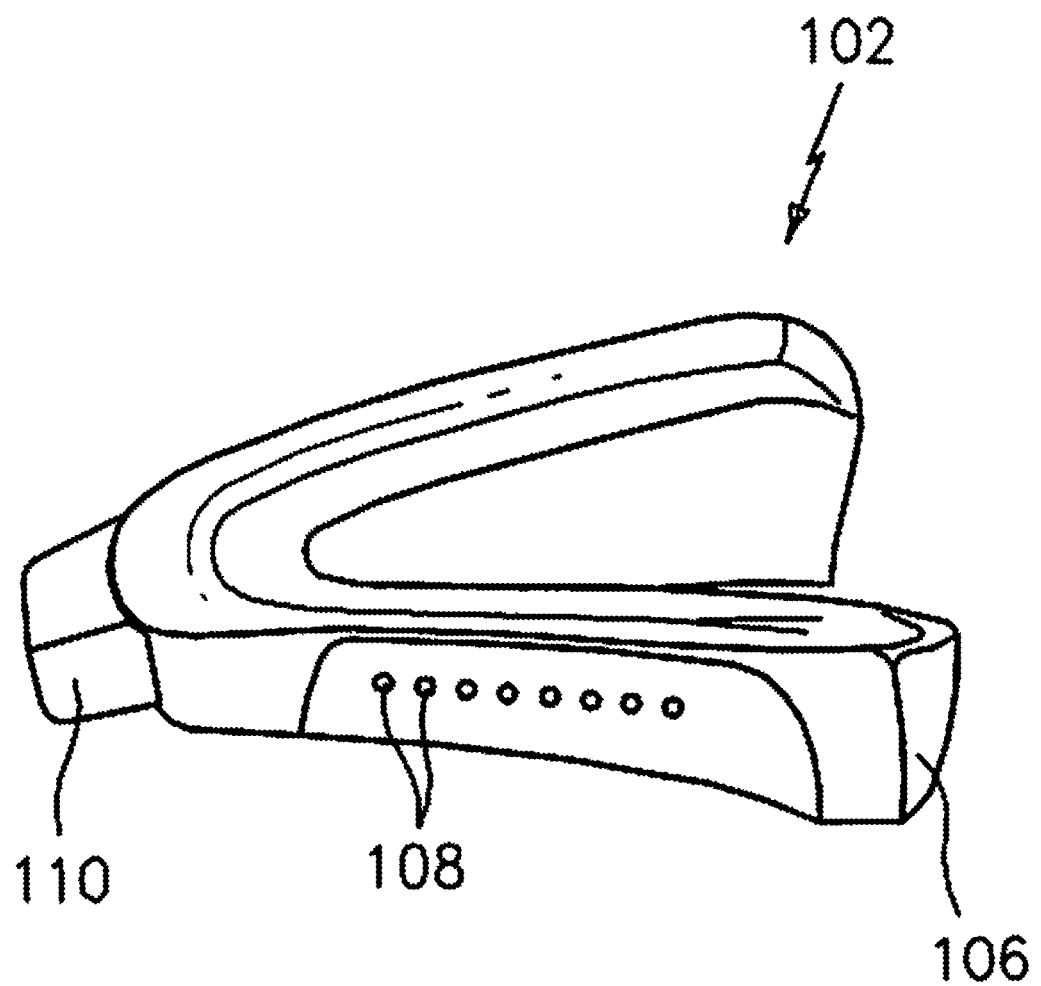

Referring initially to FIGS. 1A and 1B, the diagrams illustrate a side view of separated upper and lower dental arches, according to an embodiment of the prior art. An upper dental arch 102 and a lower dental arch 104 were formed by a series of casting and molding processes common to the art resulting in upper and lower overlays constructed to conform to the patients upper and lower teach and adjacent surfaces. In the embodiment shown in FIG. 1, the upper dental arch 102 includes a first non-deformable dental encasing component 106 that encases all the upper teeth of the patient. Alternative embodiments (not shown) may encase only a portion of the teeth as is necessary for the oral appliance to be held in place and still operate effectively. The first (lower) dental encasing component 106 includes a lingual surface and a labial surface. The lingual surface is an interior wall of the first dental encasing component that covers at least the interior side of the teeth next to the patient's tongue. The labial surface is an exterior wall of the first dental encasing component that covers at least the exterior side of the teeth next to the patient's lips.

The first dental encasing component 106 has a plurality of apertures 108 running along an anterior-posterior direction on one or both labial sides of the first dental encasing component 106. A ledge component 216, which is shown in greater detail in FIGS. 2 and 3, may be detachably fixed to the first dental encasing component 106, using at least one of the apertures 108. The plurality of apertures 108 allows the ledge component 216 to be disposed in a plurality of different lateral positions along a side of the first dental encasing component 106. More specifically, the plurality of apertures 108 allow for versatility in treating a patient because the ledge component 216 can be positioned according to the needs of a specific patient, and may be changed during a patient's treatment.

The upper dental arch 102 is also shown with a tubing adaptor 110 that may be disposed at the front, or anterior portion, of the first dental encasing component 106. The tubing adaptor 110 holds a tube (not shown) in place and provides a means to guide air or oxygen through the upper dental arch 102 and into the patient's mouth, allowing for further improvement in the treatment of snoring and obstructive sleep apnea.

The tube may be connected to an oral pressure appliance, which provides a pressurized gas stream to reduce an airway obstruction. Providing increased air or oxygen into the mouth quickly satisfies a demand for more air or oxygen resulting from a more open airway provided by placement of the oral appliance, and reduces further airway collapse which can be caused by the suction forces of the lungs. The oxygen or air from the oral pressure appliance is typically provided by a tank of pressurized gas through a tube that fits into the tubing adaptor 110. The size of the airway opening relative to tubing results in an increase in velocity of air or oxygen, provided to the lungs by virtue of a Venturi Effect.

The tubing adaptor 110 can be integral with the first dental encasing component 106, or may be detachably fixed to the first dental encasing component 106. When the tubing adaptor 110 is detachably fixed to the first dental encasing component 106, the upper dental arch 102 may be utilized with or without the tubing adaptor 110 attached.

The lower dental arch 104 includes a second dental encasing component 112 that is formed to encase the patient's lower teeth or as many teeth as necessary for the oral appliance to be held in place and still operate effectively. A rotating body 114 is rotatably fixed on both sides of the second dental encasing component 112. The rotating body 114 rotates around a pivot point 115 attached to the second dental encasing component 112. The rotating body 114 has a curved upper portion and a flat lower portion. This shape allows the rotating body 114 to extend upwardly beyond the lower teeth of the patient while not extending lower than the second dental encasing component 112. Further downward extension of the rotating body 114 would cause discomfort to the gums of the patient.

Figure 2:
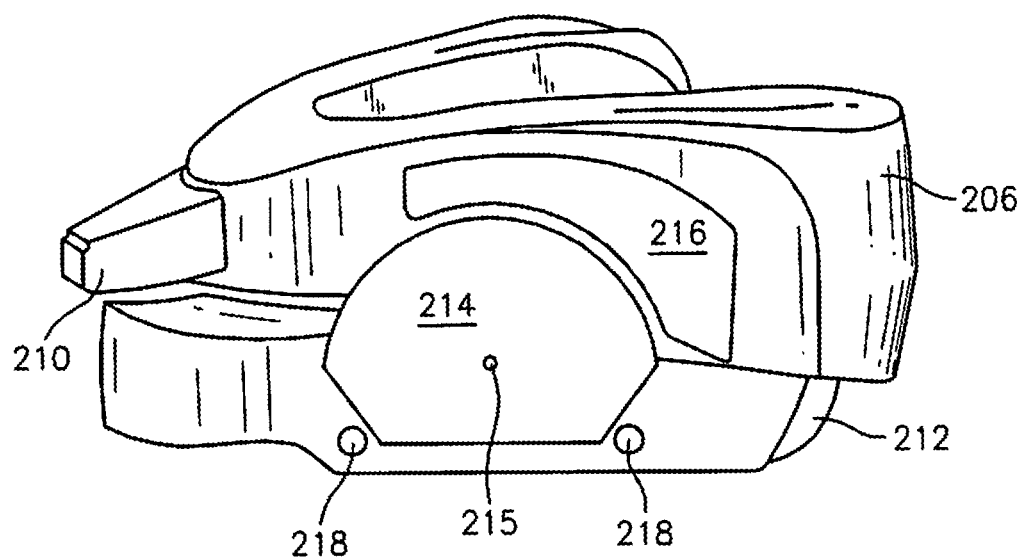
FIG. 2 is a diagram illustrating a side view of upper and lower dental arches of the prior art an oral appliance, shown in FIGS. 1A and 1B.

FIG. 2 illustrates a side view of the assembled upper and lower dental arches of an oral appliance, according to an embodiment of the prior art. A first dental encasing component 106 is shown having a tubing adaptor 110 disposed at a front anterior portion of the first dental encasing component 106, and a ledge 216 is disposed on a side of the first dental encasing component 106. An additional ledge 216 may be disposed on an opposing side of the first dental encasing component 206. The ledge 216 may be integrated into the first dental encasing component 106 or the ledge 216 may be a separate attachment. When the ledge 216 is a separate attachment, it may be detachably fixed to the upper dental arch through the use of apertures 108 shown in FIG. 1. Further, ledge 216 may be positioned and adjusted laterally in an anterior or posterior direction according to the needs of the patient. The ledge 216 has a curved surface extending from an upper, more anterior portion of the first dental encasing component 106 to a lower, more posterior portion of the first dental encasing component 106. In the embodiment shown, the ledge 216 has an integrated groove that allows for engagement with another surface, namely the rotating body 114.

A second dental encasing component 112 is shown having a rotating body 114 rotatably fixed at a pivot point 115 to a side of the second dental encasing component 112. The second dental encasing component 112 also has a pair of projections 218 that are positioned to limit the rotation of the rotating body 114. An additional rotating body 114 and pair of projections 218 may be disposed on an opposing side of the second dental encasing component 112. The rotating body 114 is disposed for engagement with the ledge 216 of the upper dental arch 106. More specifically, as a patient's mouth closes, the rotating body 114 rotates along the curved surface of ledge 216, advancing the mandible forward. This rotation along the surface of the ledge provides additional ease in advancement. The projections 218 limit the rotation of the rotating body 114 in accordance with the patient's needs. Further, the projections 218 prevent rotation of the rotating body 114 into the lower gums of the patient. In the prior art embodiment, the surface of the rotating body 114 also engages the integrated groove in the ledge 216 so that the rotating body 114 may not slip laterally off the ledge 216 during rotation.

The ledge 216 and the rotating body 114 are both specifically shaped in accordance with the needs of the patient. For example, the ledge 216 and the rotating body 114 are shaped with a curvature that follows a smooth and natural mouth closing motion of the patient while still advancing the mandible forward. The guided closure of the patient's mouth is also affected by the limited rotation of the rotating body 114 according to where the projections 218 are set. More specifically, the rotating body 114 allows for movement of the jaw while maintaining the necessary protrusion of the mandible. The steepness of the degree of advancement as well as the amount of maximum mandibular protrusion are controlled by the changing curvature and position of the rotating body 114. Further, the rate of mandibular advancement may start slowly, then increase toward a mid-position, then slow the rate of advancement at the end of the mandible's maximum protrusion. This places less stress on the TMJ. More customization is possible to further reduce tension on the TMJ by transcribing the patient's jaw motion to the shape of the rotating body 114. This offers the least stress on the TMJ, while advancing the jaw to its appropriate position.

Figure 3:
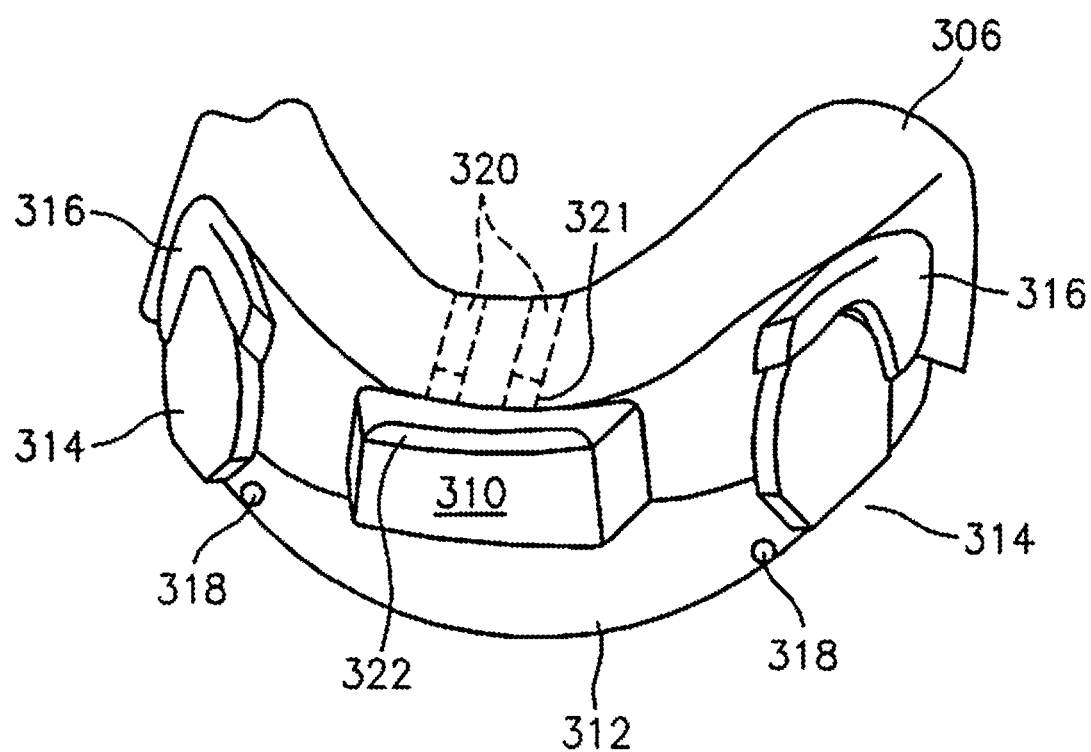
FIG. 3 is a diagram illustrating a front view of upper and lower dental arches of the prior art oral appliance of FIGS. 1A and 1B.

FIG. 3 is a front perspective view of upper and lower dental arches of the prior art oral appliance, according to an embodiment of the present invention. A first dental encasing component 106 is shown with two ledges 216 and a tubing attachment 110. A second dental encasing component 112 is shown with two rotating bodies 114 and projections 218. The tubing attachment 110 is attached to tunnels 320 provided through the first dental encasing component 106 that allow air or oxygen to flow from a tube into the mouth of the patient. The tunnels 320 guide air or oxygen into the first dental encasing component 106, around the patient's teeth, and exit at the interior of the patient's mouth. The tubing attachment 110 is preferably attached by inserting open projections 321 of the tubing attachment 310 into the tunnels 320 of the first dental encasing component 106. Further, the tubing attachment 110 includes a groove 322 across its front in which the tube may be detachably held when air is being guided into the mouth of the patient. The front groove 322 guides air into the tubing attachment 110, out the open projections 321 and into the tunnels 320. The tubing attachment 110 may also be integrated into the first dental encasing component 106.

The embodiments of the prior art described above provided an appliance that improves the manner and ease of mandibular advancement through the use of a rotating body, and also provided versatility during treatment through possible adjustments. The embodiments of the present invention also provide for adaptation of the appliance for use with oral pressure appliances. The mandibular advancement and increased airflow provide a patient with greater success in eliminating snoring and sleep apnea. However, that oral appliance required multiple visits to first cast molds of the patient's teeth, a separate fabrication process to form the appliance, and then one or more office visits to fit and possibly modify the oral appliance.

To produce an oral appliance as described above, the following materials were used and a typical process to fabricate the device is as follow. First, a single bite impression of the patient's upper and lower teeth is first prepared using a material such as silicon putties or alginate. A bite registration mold may also be prepared. The single bite impression and the registration impression is then sent to a lab for the casting of a Plaster of Paris (or similar hard material) to form a cast of the upper and lower arch which are assembled to provide a model of the patient's actual teeth and upper and lower registration. The appliance is then fabricated from Biocryl or other similar thermoplastic materials, for example by a Vacuform type procedure to heat and mold the plastic material around the previously produced model of the patient's teeth. The wings, cams and cam plate are attached using self curing acrylic. Positioning of the upper and lower interactive arches are thus fabricated to match the anatomic soft tissue and teeth in the cast model. However, any errors in fitting generally require preparing a new bite mold and a new casting.

In contrast to the above described prior art oral appliance, an appliance, referred to as a two-piece moldable wing design, incorporating features of the current invention is shown in FIGS. 4-9.

The two-piece wing design is different in several respects from the above described prior art device. That new oral appliance comprises a preformed, multiple-piece lower arch constructed out of injection molded, medical grade polycarbonate. The preformed arch provides a substrate for the over molding of a flexible Polycaprolactone material. This material can be shaped and molded directly on the patient in the dentist's office in a single sitting to conform to the to the patients lower and upper teeth.

Figure 4:
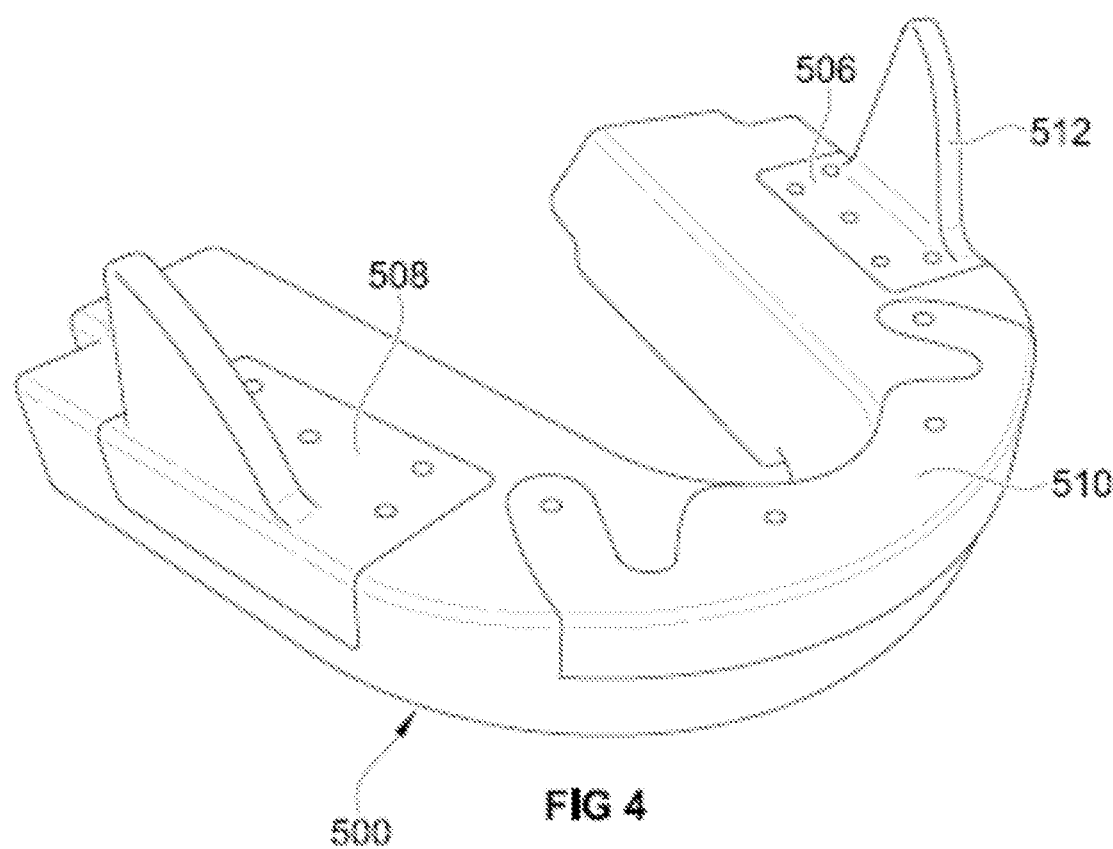
FIG. 4 is a top perspective view of a lower dental arch incorporating features of the invention.

Polycaprolactone is a polyester with a low melting point of around 60° C. (140° F.) and a glass transition temperature of about −60° C. (−76° F.). As a result, it can be softening at a safe elevated temperature, formed by hand in the patient's mouth, and then cooled to create a rigid arch solid at body temperature and can be reheated and reshaped. That lower arch 500 has three portions, each portion having a higher melting temperature material, such as polycarbonate, attached thereto. As shown in FIG. 4, and the exploded view in FIG. 8, the substrate has left and right winged stiffeners 506, 508 and a forward stiffener 510 attached thereto and integral with the preformed but reshapable over mold, comprising the lower dental arch 500.

Figure 5:
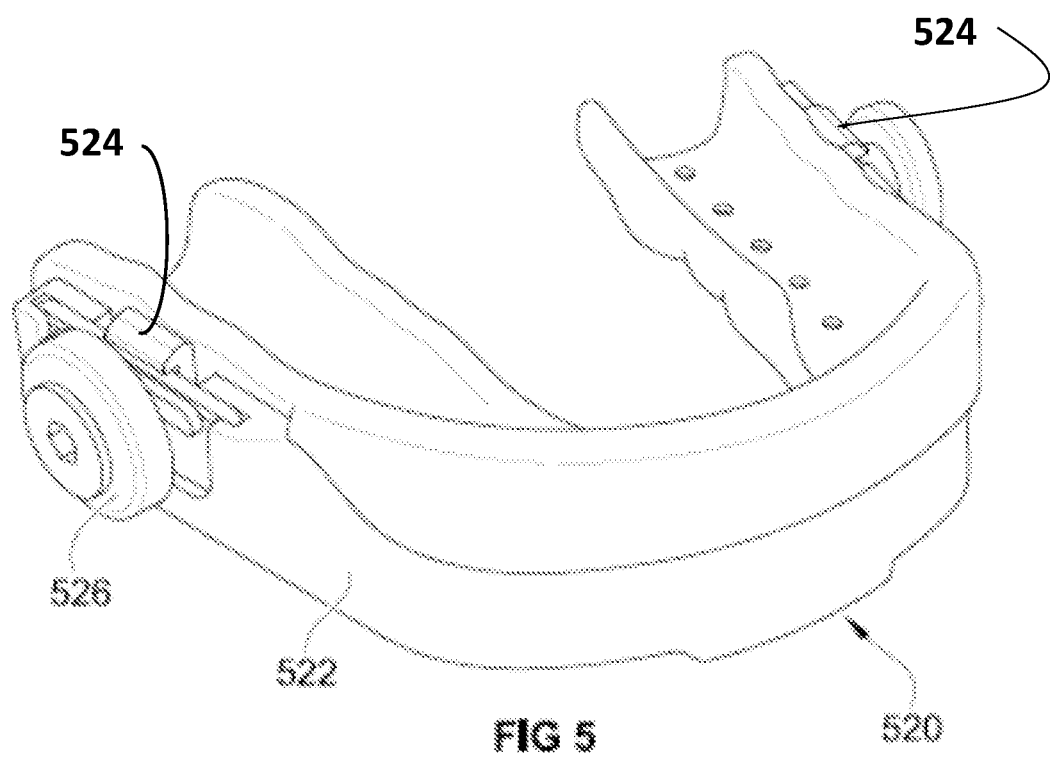
FIG. 5 is a top perspective view of an upper dental arch incorporating features of the invention, the figure showing a cam for connection to a portion of a lower arch.
Figure 9:
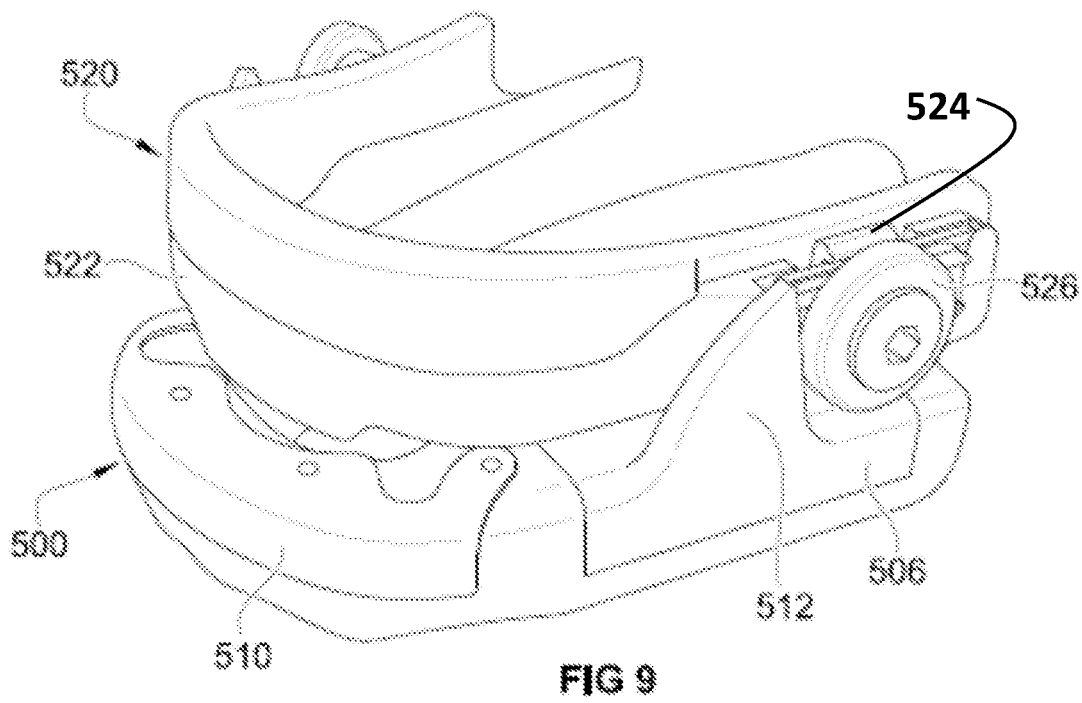
FIG. 9 is a perspective view of the lower and upper arch portions assembled together.

The deformable arch over mold can be heated at, a sufficiently low temperature and soften at approximately 135° F. to about 160° F., so that the heated, softened arch can be placed in the patient's mouth while warm so it can be manipulated to conform to the shape and size of the lower and upper portion of the mouth and teeth before it cools sufficiently, for example to body temperature, at which temperature it retain its shape. Preferably the arch is not heated above about 180° F. to avoid burning the patient's mouth by inserting an arch into the patient's mouth while it is at too high a temperature. The three lower substrate pieces are shaped and positioned to allows the over-mold to be stretched and bent during the molding process. The material used for these three parts is strong, and will control the shape and amount of deformation the over-mold will provide. The current stiffener/substrate are designed to handle the forces that are created between the wheels (cams) and wings, while maintaining the necessary mandibular advancement. Their shape allows for the necessary softening and molding of the over-mold to adapt to varying shape and sizes of the dental arch. When positioned in the mouth along with an upper arch, the wings 512 are in a cooperative, interactive relationship with the wheels (cams) 526 of the upper unit (described below), advancing the patient's jaw forward, the wheels 526 being held on the stiffener 522, as shown in FIGS. 5 and 9 by locking pins 524. Upon cooling the device maintains the new size and shape.

An upper arch 520, shown in FIG. 5, is also formed from the same or similar flexible and formable material, such as polycaprolactone. Integral with the preformed upper arch is a one piece stiffener 522, shown as a separate component in FIG. 6. While shown as a single piece; the stiffener, like the lower arch, can also be provide as several, preferably three, separate pieces to allow more flexibility in conforming the upper arch 520 to the upper teeth.

Figure 6:
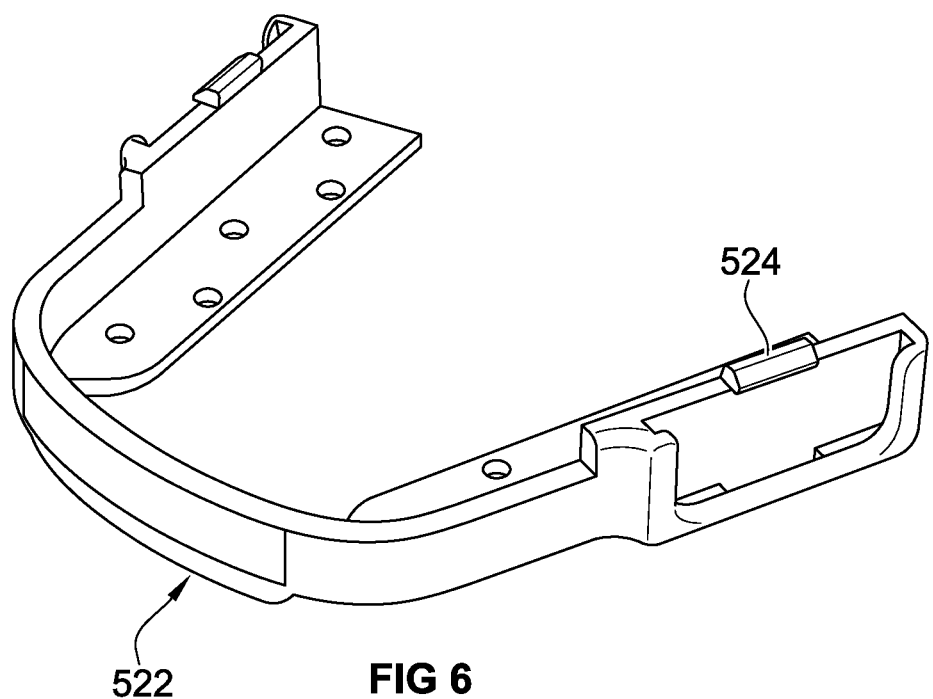
FIG. 6 is a top perspective view of a stiffening structure for the upper dental arch as shown in FIG. 5.
Figure 7:
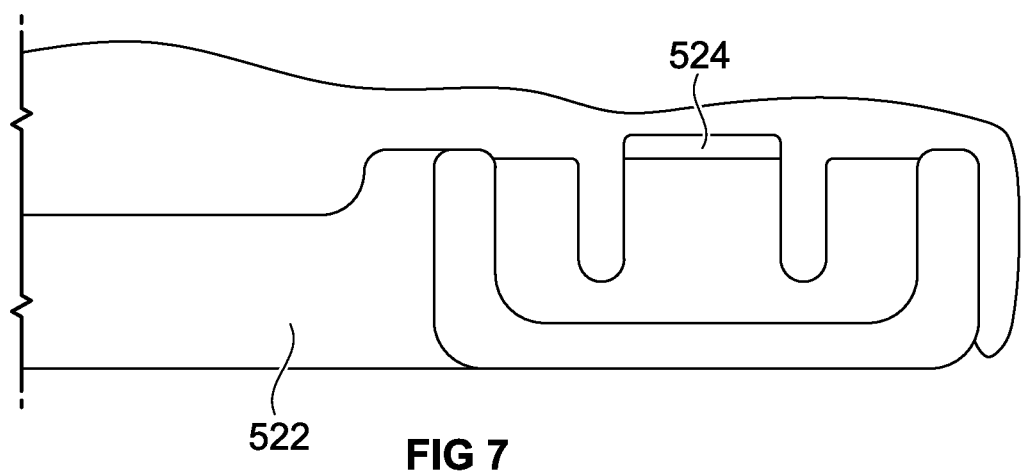
FIG. 7 is a partial side view of the stiffening structure of FIG. 6 applied to the upper dental arch as shown in FIG. 5.
Figure 8:
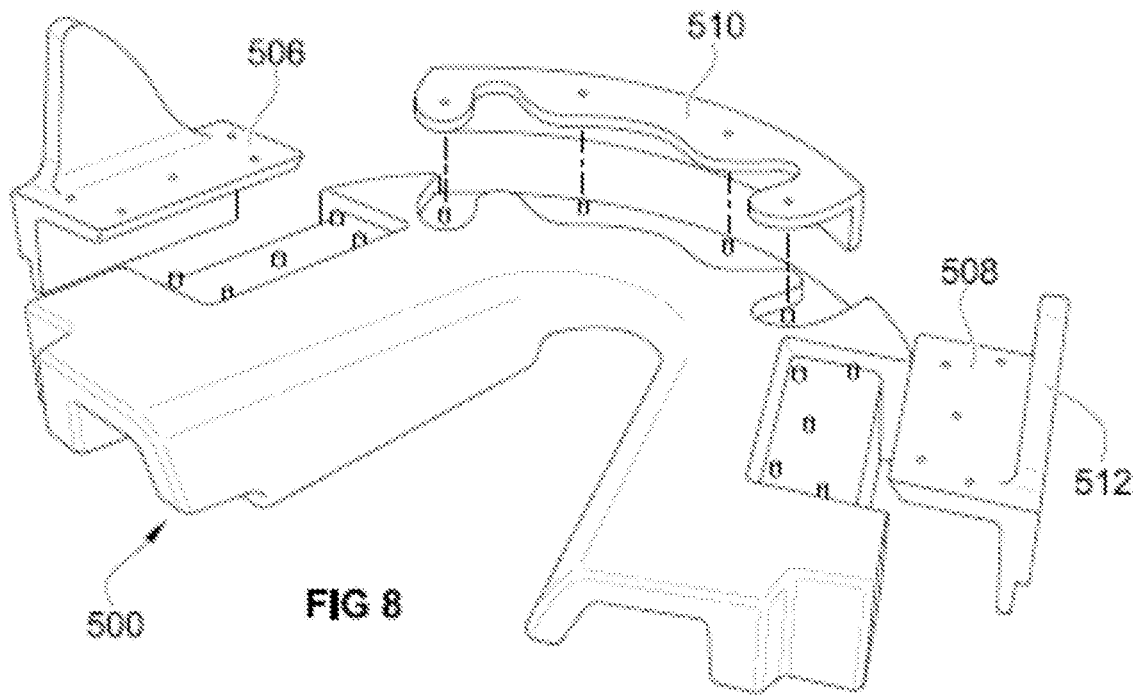
FIG. 8 is a top perspective exploded view of the overmold and substrate/stiffening structure of the lower dental arch as shown in FIG. 4.

FIG. 7 is a side view of the stiffener 522 of FIG. 6 applied to the upper dental arch as shown in FIG. 5. While shown as 1 piece, the upper stiffener can also comprise several pieces so that the upper substrate can also be more readily shaped to conform to the upper teeth. The current single piece design is shaped so that only the plastic on the labial surface of the arch is continuous. It has no lingual surface and only a small occlusal platform to support the moldable over-mold material. Since the polycarbonate plastic material is flexible, it creates an expandable clasp around the upper teeth, maintaining support. While not generally necessary, a potential advantage of forming the upper arch with at least three pieces is that the over-molded polycaprolactone, while still flexible, can be manipulated so that the wings on the lower arch can properly contact the cam structure on the upper stiffener. This provides even more accommodation a variety of naturally occurring dental arch shapes and sizes.

The upper and lower arches are assembled, heated to a flexible stage by immersion in 160° F. water and then placed in the patient's mouth and molded to the patient's upper and/or lower teeth in a single operation. Shaping and molding of the assembled arches (see FIG. 9) in the patient's mouth can also be assisted by applying sufficient elevated temperature to the arch assembly while in the patient's mouth, taking care to not elevate the temperature above that readily tolerated by the individual. One skilled in the art will readily recognize that individuals often consume heated beverages (coffee, tea, soups, etc.) so sufficient elevated temperatures can be readily tolerated by the tissue within the mouth. As pointed out above, the lower and upper arch structures 500, 520 are preformed in shapes and sizes suitable for placement preassembled in a patient's mouth so that the assembled arrangement can then be molded into a custom device in a single sitting.

By dividing the lower arch substrate into 3 units, the oral appliance can be shaped and sized once the assembly is heated and soft. This is important because the wings need to meet with the wheels (cams) 526 of the upper unit. Upon cooling the device maintains the new size and shape. While the invention has been shown and described with reference to certain preferred embodiments thereof, it will be understood by those skilled in the art that various changes in form and details may be made therein without departing from the spirit and scope of the invention.

I claim:

1. An oral appliance that controls positioning of a patient's jaw comprising:
    a first dental encasing component formed to overlay at least a portion of the patient's upper teeth, the first dental encasing component having a lingual surface, a labial surface, and a first and second wheel extending from the labial surface of the first dental encasing component;
    a second dental encasing component formed to overlay at least a portion of the patient's lower teeth and having a lingual surface and a labial surface and a first and second wing extending upward from the second dental encasing component;
    the first and second wheels fixed to the labial surface of the first dental encasing component, each positioned to enable the first wheel to contact a posterior edge of the first wing and the second wheel to contact a posterior edge of the second wing such that each wheel rotates along a length of the respective wing as the patient's mouth closes, advancing the patient's jaw forward
    the first dental encasing component and the second dental encasing component comprising a layer of an over-mold polymeric material, said over-mold polymeric material being stiff and solid at body temperature but moldable and deformable at a first elevated temperature and a stiffening material which is stiff and solid at body temperature but not deformable at a second elevated temperature of at least about 160° F.,
    one or more pieces of the stiffening material forming a substrate for the over-mold polymeric material, the combined one or more substrate pieces and over-mold polymeric material comprising the first dental encasing component, the over-mold polymeric material being permanently attached to the one or more pieces of the stiffening material to form the first dental encasing component,
    multiple pieces of the stiffening material forming a substrate for the over-mold polymeric material, the combined substrate pieces and over-mold polymeric material comprising the second dental encasing component, the over-mold polymeric material permanently attached to the multiple pieces of the stiffening material to form the second dental encasing component,
    the substrate of each of the first and second dental encasing components configured in the shape of an arch sized to respectively cover lower and upper teeth in the mouth of a patient, each of said arches, following exposure to said elevated temperature, being formable to conform to the lower and upper teeth respectively of said patient and to retain said conformation when cooled to body temperature.

2. The oral appliance of claim 1, wherein the first wing engages with a surface of the first wheel and the second wing engages with a surface of the second wheel, said wings and cams being removably attached to or integral with a portion of the first dental encasing component stiffening material.

3. The oral appliance of claim 2, further comprising the first and second wings removably fixed to a portion of the stiffening material of the second dental encasing component, said wings being configured to be in contact with the wheels on the first dental encasing component, the wheels disposed on posterior sides of the first dental encasing component for engagement with the wings on posterior sides of the second dental encasing component.

4. The oral appliance of claim 1 wherein the polymeric over-mold material comprises polycaprolactone or a low melting temperature acrylic film.

5. The oral appliance of claim 1 wherein the first elevated temperature is from about 135° F. and 160° F.

6. An oral appliance for repositioning the lower teeth and lower jaw of a patient into proper alignment with the patient's upper teeth comprising:
   a first dental encasing component formed to overlay at least a portion of the patient's upper teeth and a second dental encasing component formed to overlay at least a portion of the patient's lower teeth, said dental encasing components each comprising one or more sheets of a moldable and flexible over-mold material, said over-mold material having attached thereto multiple pieces of a stiffening material, the over-mold material after heating to an elevated temperature being moldable and shapeable within the patient's mouth but being non-deformable once cooled to body temperature, said stiffening material after being heating to the same elevated temperature not being moldable nor deformable within the patient's mouth,
   the stiffening material of the first dental encasing component having a rotatable wheel portion attached thereto and the stiffening portion of the second dental encasing component having a wing portion mounted vertically thereto, the rotatable wheel portion in contact and interacting with a posterior edge of the wing portion to advance the patient's jaw forward as the patient's mouth is closed.

7. The oral appliance of claim 6 wherein the elevated temperature is not greater than about 160° F.

* * * * *